(12) United States Patent
Spartz

(10) Patent No.: US 10,024,749 B2
(45) Date of Patent: Jul. 17, 2018

(54) METHOD AND SYSTEM FOR LEAK RATE TESTING OF PRESSURIZED CONTAINERS

(71) Applicant: MAX Analytical Technologies, Inc., East Windsor, CT (US)

(72) Inventor: Martin L. Spartz, Ellington, CT (US)

(73) Assignee: MAX Analytical Technologies, Inc., East Windsor, CT (US)

( * ) Notice: Subject to any disclaimer, the term of this patent is extended or adjusted under 35 U.S.C. 154(b) by 0 days.

(21) Appl. No.: 15/465,395

(22) Filed: Mar. 21, 2017

(65) Prior Publication Data

US 2017/0299459 A1    Oct. 19, 2017

Related U.S. Application Data

(60) Provisional application No. 62/321,835, filed on Apr. 13, 2016.

(51) Int. Cl.
G01M 3/02     (2006.01)
G01N 21/3504  (2014.01)
G01N 21/35    (2014.01)

(52) U.S. Cl.
CPC .......... G01M 3/02 (2013.01); G01N 21/3504 (2013.01); *G01N 2021/3595* (2013.01)

(58) Field of Classification Search
CPC ...... G01N 21/3504; G01N 2021/3595; G01M 3/04
See application file for complete search history.

(56) References Cited

U.S. PATENT DOCUMENTS

| | | | | |
|---|---|---|---|---|
| 2008/0060421 A1* | 3/2008 | Muller | ................. | G01M 3/229 73/49.2 |
| 2009/0231707 A1* | 9/2009 | Ehm | ..................... | B82Y 10/00 359/509 |
| 2012/0037796 A1* | 2/2012 | Lehmann | .............. | G01M 3/202 250/282 |
| 2015/0260695 A1 | 9/2015 | Spartz et al. | | |

* cited by examiner

*Primary Examiner* — David Porta
*Assistant Examiner* — Faye Boosalis
(74) *Attorney, Agent, or Firm* — HoustonHogle LLP

(57) ABSTRACT

A leak rate testing system for pressured containers such as inhalers includes a test chamber holding the pressurized containers and accumulating compounds leaking from the containers. A sample cell receives the compounds from the chamber and a spectroscopy system obtains spectral responses of compounds in the sample cell so that a controller can determine leak rates over time.

24 Claims, 1 Drawing Sheet

METHOD AND SYSTEM FOR LEAK RATE TESTING OF PRESSURIZED CONTAINERS

RELATED APPLICATIONS

This application claims the benefit under 35 USC 119(e) of U.S. Provisional Application No. 62/321,835, filed on Apr. 13, 2016, which is incorporated herein by reference in its entirety.

BACKGROUND OF THE INVENTION

In the manufacture and distribution of pressurized containers, it is often necessary to detect the rate at which gas leaks from the containers. The characterization of leak rates is especially important in the manufacture of pressurized containers for medication, such as inhalers. Here, leak rates can impact such metrics as the number of dosages, expiration dates, and efficacy. Over time, loss of propellant from a metered dose inhaler (MDI), for example, can result in increased concentrations of the active ingredient, leading to a larger than intended drug quantity being administered.

In the past, infrared spectrometry has been used to estimate leak rates of inhalers. The gases leaking from inhalers were passed through the sample cell of an infrared spectrometry system. From this information, the leak rates could be estimated.

SUMMARY OF THE INVENTION

With improvements in the manufacturing of inhalers, the leak rates have dropped and the consistency between each inhaler has improved. Nevertheless, the leak rates must still be characterized and the manufacturing of the inhalers must be monitored, especially for product safety and to ensure compliance with governmental agency (Food and Drug Administration (FDA)) rules governing drug manufacture.

The present invention concerns a system and method for measuring leak rates, such as leak rates for inhalers. Individual pressurized containers or shipping boxes of pressurized containers are placed in a test chamber, which is airtight or substantially airtight. Gases, such as air from the test chamber, are then circulated through a sample cell of a spectrometry system, such as a Fourier transform infrared (FTIR) spectrometry system.

The present invention leverages a closed loop flow path that allows contents leaking from a pressurized container to build over time. In many cases, smaller loops are preferred.

Whereas many other instruments destroy the analyzed sample when the sample hits the detector, the present system keeps probing the concentration by passing the IR beam through its gas cell.

The spectrometry system is used to characterize the leak rate of the containers. Specifically, the spectrometry system determines spectral response of compounds, e.g., gases within the test chamber. A control system then compares the spectral response to the known spectral response of one or more contents of the containers and a background spectrum is captured usually at the beginning of the test. This enables the control system to determine the instantaneous concentration of the container contents in the test chamber. Knowing the test system volume, the leak rate for the containers is then determined.

An important aspect of the invention is placement of the containers in a test chamber. This allows the container contents leaked from the pressurized container(s) to accumulate in the test chamber. As a result, with the passage of time, the concentration of the container contents in the test chamber increases, enabling the characterization and estimation of even very low leak rates.

The above and other features of the invention including various details of construction and combinations of parts, and other advantages, will now be more particularly, described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
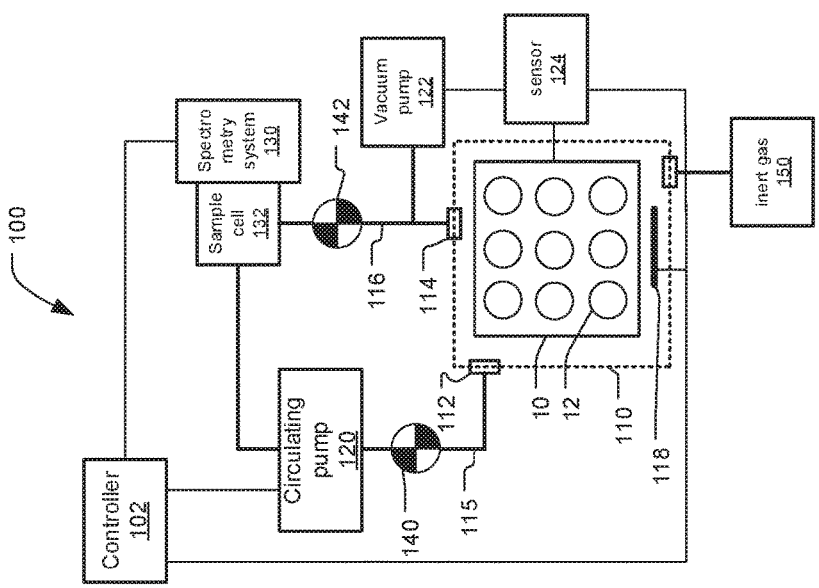
FIG. 1 is a schematic diagram of a pressurized container leak rate testing system according to the present invention.

FIG. 1 shows a leak rate testing system 100 which has been constructed according to the principles of the present invention.

In the illustrated example, a unit 10, a shipping box, for example, of inhalers 12 is placed in a test chamber 110 of the leak rate testing system 100. Individual inhalers also can be monitored in test chamber 110, as can be one or more pressurized containers other than inhalers, e.g., pressurized spray cans, aerosol cans under pressure, pressurized gas bottles, lecture bottles, for example, and the like. In the preferred embodiment, the test chamber 110 is an airtight chamber that has a top lid or door that can be opened to enable the placement of the shipping box 10 within the test chamber 110. Then the door or lid can be sealed shut to thereby form the airtight, or substantially airtight, chamber.

In the illustrated example, the test chamber 110 has an outlet port 114 and an inlet port 112. Each of these ports is connected via corresponding piping 116, 115 to valves 142, 140, respectively. On the path between the outlet port 114 and the inlet port 112 are a sample or gas cell 132 and preferably a circulating pump 120, such as diaphragm pump. As a result, when the valves 142, 140 are opened, the activation of the circulating pump 120 draws air from the outlet port 114 through the outlet port valve 142 through the sample cell 132 and then returns the air through the inlet port valve 140 and the inlet port 112 back into the test chamber 110.

The system 100 includes a spectrometry system 130 for spectrally analyzing and detecting components of a sample stream flowing through the sample cell 132. In different implementations, the spectrometry system determines the spectral response of the components in the sample cell 132 in one or more of the following spectral regions; millimeter, microwave, terahertz, infrared (including near-, mid- and/or far-infrared), visible, ultraviolet (UV), x-rays and/or gamma. Further, the spectrometry system can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra of the components in the sample cell 132.

In the case of optical spectrometry systems, for example, different technologies can be employed. In FTIR systems, single beam spectra are generated by taking the raw interferograms from the FTIR spectrometer. Then, the controller 102 converts those interferograms to intensity versus wavenumber spectra. Then, sample and background single beam spectra are used to create the absorbance spectra. In other situations, spectra might be more directly read-out as in the case where the spectrometry system 130 is a post dispersive system, which includes a broadband source and a spectrally resolving detector system. In other examples, the spectrometry system 130 includes a tunable optical source (e.g., tunable laser) and a detector. Here, the spectral information is a function of the time response of the detector, in such a pre-dispersive, spectrometry system.

In general, the spectrometry system 130 is preferably sufficiently sensitive to detect the contents of the pressurized containers 12 at low concentration, such as low parts per million (ppm) to parts per billion (ppb) concentrations. Identified components' concentrations are detected and analyzed by the spectrometry system 130 and the controller 102.

Sample or gas cell 132 is provided with windows made of $BaF_2$, $CaF_2$, or another suitable material and can be configured for multiple-path (also known as multiple-pass or long path) absorption. By increasing the path length traveled, multiple-pass arrangements can be used to measure low concentration components or to observe weak absorption spectral features without increasing the physical length or volume of the cell itself. Since the detection limit of the system is directly related to the volume/path length ratio, decreasing the volume or increasing the path length lowers the concentrations that can be detected. Assuming no signal losses, doubling the path length or reducing the volume ire half will lower the detection limit by a factor of 2.

In certain embodiments, longer path lengths are used in combination with higher reflective coatings like enhanced silver, yielding a reflectivity in the 0.992 to 0.995 range or greater. Coating optimizations, in the IR region, for example, could further improve reflectivity. This allows for pathlengths that are longer by a factor or 4 to 8 or even more.

In specific implementations, sample cell 132 is configured as a "White cell" type. The principles of a traditional White cell arrangement employ three spherical concave mirrors having the same radius of curvature. These principles can be modified, to improve image quality and optical throughput, as described, for instance, by Spartz et al. in U.S. Patent Application Publication No. 2015/0260695 A1, with the title Process and System for Rapid Sample Analysis, published on Sep. 17, 2015 and incorporated herein by reference in its entirety. In one example, the White cell type employed uses non-spherical concave mirrors cut onto a single metal or a glass blank, providing a fixed path length; the mirrors can be the solid end caps of the sample cell, allowing for smaller sample cells that are easier to align.

Other multiple pass cell designs that can be utilized include but are not limited to Herriott cells, Pfund cells, cavity-ring down cells, and integrating spheres.

In still other examples, the gas cell is arranged in the headspace above the pressurized containers 12 and/or the shipping container 10 in the test chamber 110.

The gas flow is through the sample cell 132 and is controlled by the pump 120. In some cases, the flow rates are not critical. The system can operate with a wide range of flow rates. Nevertheless, the higher flow rates, such as 100 mL/min or higher, provide better mixing. In other examples, lower flow rates of 1 mL/min., or less can be used. The low flow rate is a possibility since the tests will usually run over days or weeks.

In one embodiment, a heater 118 is provided to heat the test chamber 110. Other components in the flow path can be heated. In some cases, the entire flow path, from test chamber 110, through the outlet port 114, outlet port piping 116, the outlet port valve 142, the sample cell 132, the circulating pump 120, inlet port valve 140, and the inlet port 112 is heated, e.g., by heater 118 and/or other suitable heating means. This feature is particularly useful when analyzing compounds with varying vapor pressures or boiling points, e.g., measuring semi-volatile or even nearly non-volatile compounds.

In examples, the heater 118, used for heating test chamber 110, for instance, includes but is not limited to heating tape, heating jackets, ovens, Peltier heaters/coolers, cartridge, immersion, and so forth. The temperature of the test chamber 110 can be held at an elevated level such as greater than 40° C. or 60° C. or higher in order to perform accelerated aging tests on the containers or inhalers 12.

In one implementation, the individual pressurized container(s) 12 or shipping box 10 housing containers 12 are placed in test chamber 110. The test chamber 110 is then first purged with a gas, such as nitrogen, supplied, for instance, from gas source 150. Inert gases such as helium or argon or another suitable gas or combinations of gases also can be employed. In some cases, the test is performed with air in the test chamber 110. However, by purging the whole system with nitrogen ($N_2$), lower detection limits will generally be achieved because the system can then run at lower resolution and get higher signal to noise ratios (SNR).

In other examples, the test chamber 110 is partially evacuated to an internal gas pressure lower than the surrounding (atmospheric or ambient) pressure. In specific implementations, the pressure in the sample cell is within the range of 0.9 to 0.1 atmospheres (atm) in order to perform stress tests or accelerated aging tests or test the performance at altitudes such as would be experienced at some high altitude cities or on airplanes. The pressure is reduced with vacuum pumping device 122, e.g., a traditional foreline oil pump, a diaphragm pump or another suitable pump or alternative apparatus capable of drawing a vacuum. The pressure in the sample cell 132 or the chamber 110 can be monitored by the controller 102 with a sensor 124, such as, for instance, an absolute pressure sensor.

Figure 2:
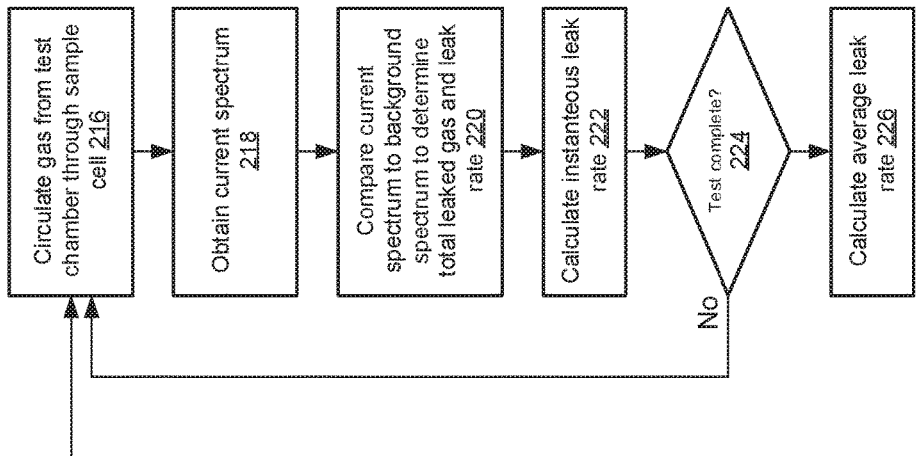
FIG. 2 is a flow diagram illustrating the operation of the system according to the present invention.

FIG. 2 shows operation of the system according to one embodiment.

Initially, in step 205, the system 100 is preferably purged with an inert/non-reactive gas such as nitrogen from gas source 150. In general, a gas is chosen that is different from any gases contained in the inhalers 12. So, if nitrogen is used as a carrier gas in the inhalers, then possibly helium is used, for example.

Then, in step 210, gases from the test chamber 110 are circulated through the sample cell 132 under the control of the controller 102. This is achieved by opening the valves 140, 142 and activating the circulating pump 120 to further purge the system 100.

During operation, gas is captured in the sample cell 132 for a specific time, based on the gas turnover rate in the sample cell. Various flow conditions can be employed. In a continuous mode, for instance, the entire experiment (run) is conducted under a set, i.e., unchanging pressure and flow rate through the cell. In a transient mode, the circulating pump is run intermittently to load a new sample of gas into the sample cell 132 when a new sample is to be taken. In any event, the controller 102 preferably continues to measure spectra and continues to flow the gas to monitor the slope change of the compound concentration.

Specifically, in step 212, the baseline, background spectrum is acquired. Then the shipping box 10 of inhalers 12 is sealed in the test chamber 110 in step 214. However, in some cases, the background spectrum is captured just after the test chamber 110 is sealed.

During the test, gas from the test chamber 110 is circulated through the sample cell 132 by the circulating pump 120 and then returned to the test chamber via the inlet port 112.

On a periodic basis, the current spectrum is obtained in step 218.

The controller compares this spectrum to the background spectrum to determine change in the contents concentration in step 220 and thereby calculate the leak rate based on the total time that the chamber 110 has been sealed, the total volume of the test system 100, and the time that the test has been running. This allows the controller 102 to calculate the average and instantaneous leak rate in step 222.

In step 224, the controller 102 determines whether or not the test is completed. In some cases, the test will be a relatively short test. In one example, the test runs for less than a day, such as 2-3 hours or less. In other examples, longer-term performance data are required. Specifically, the test can then be run for a day, several days, a week or longer.

In one mode of operation, the FTIR is operated to maximize its sensitivity. Specifically, low resolution and longer scan times are used to obtain the spectra. In one example, the scan time of the FTIR spectrometry system 130 requires over a minute to acquire a spectrum.

In any event, if the test is not completed, gas continues to circulate through the sample cell 132 from the test chamber 110 and new spectra are acquired by the spectrometry system 130. However, if the test is completed, then an average leak rate can be calculated in step 226 by the controller 102.

The amount of averaging for background and sample spectra can be application dependent and dependent on the total length of the test. In one example, the spectra are generated using 1 minute (min. averaging or longer.

The controller 102 further preferably monitors the pressure detected by the pressure sensor 124 and/or the output of other sensors/transducers. In specific examples, the controller 102 accesses internal or external libraries, and/or other devices or sources needed for data collection and analysis or to correct for pressure changes.

With respect to data handling (e.g., data collection and analysis), a process carried out by the controller 102 can involve: data collection; data integral/differentiation/signal averaging, data spectral deconvolution/quantification; data reporting; and others. Each function can be controlled through methods such as further described below.

In one example, a suitable configuration for data collection has a resolution (with cosine apodization) of 4.0 cm$^{-1}$. As known in the art, apodization can be used to change the shape of a mathematical function, an optical transmission or a mechanical structure. In the system and method described herein, apodization is particularly important for obtaining spectra without artifacts when very low noise spectra are desired. For example, an apodization function that goes to zero appears to make a significant difference in baseline artifacts. Valuable information also can be obtained using higher or lower resolutions. In some cases, protocols are used for calibrations that are stable from instrument to instrument or over time. For instance, constant calibration of the detector can be implemented with a suitable detector linearization algorithm.

An illustrative configuration has about 34 co-added scans that can take about 5 seconds.

Multiple region analysis for optimal fit and analysis can be employed. For example, software can be designed to select one, more or all absorption regions present in an IR spectrum for optimized analysis and precision. In specific examples, the software is set to manually select all the compounds to be analyzed and their respective analysis regions to be used. Preferably, when multiple compounds are present, a matrix for the compounds present is built and used to analyze the current spectra.

Data reporting by the controller 102 can include information such as compounds identification, level of sample concentration, and original concentrations of sample (before concentration), "goodness" of fit of spectral match. Typically, the key metrics are the starting concentration and ending concentration of the analyte that is leaking. The analyte is a compound or combination of compounds present in the pressurized container being tested, such as, for instance, one or more active and/or inactive ingredient(s) found in an inhaler. Specific examples include but are not limited to one or more gases (e.g., a product, a carrier gas, a propellant, etc.) and/or one or more vapors (e.g., volatile organic compounds (VOCs)) or vapors generated from semi- or non-volatile substances heated by heater 118. Other examples use analytes serving as tracers added to the usual contents of a pressurized vessel to facilitate detection by the spectrometry system employed. In the case of a leak, the analyte seeps into test chamber 110, accumulates and is detected as described herein.

The difference between the starting and end-point concentrations is then compared to the time change or the length of time over which the test was run. The volume test system 100 including the volume of the test chamber along with the tubing 115, 116 and sample cell 132 are used to find the mass change versus time. The controller 102 reports that change or some form of mass versus time to thereby characterize the cumulative leak rate for the inhalers 12.

In many implementations, data analysis is conducted during the data collection process. In specific examples, the process includes one, more or all of the features described below.

Standard drivers for the spectrometer's controller 102 can be utilized during spectra collection, a process that typically includes obtaining a background spectrum. In many cases, this background spectrum is an average of spectra determined by the controller 102 for ~1 and 2 minutes.

IR spectra will then be collected by the controller 102 at a nominal spacing, for example, every 5 seconds. While the spacing could change during the experiment, this is not necessary since the data will be averaged after collection by the controller 102. Typically, therefore, spectra can be collected at the same spacing from beginning to the end of the sampling, with 2 seconds providing good resolution in many cases. More generally, however, these time periods are leak rate dependent. If it is a very low leak rate, there is no need to collect fast data: 1 minute averages or longer are preferably used. If there is a very fast leak rate, scan times in seconds could be used for better precision, on the other hand.

Again, each reported spectrum will be an average of IR spectra over that time frame. While the same number of data points will be present, after the initial few data sets they will be averaged spectra determined by the controller 102. Averaging can take place in Igram, Single Beam or Absorbance space and comparisons can be undertaken to determine which results in the best SNR by the controller 102.

If the data are collected by a FTIR, the raw interferograms will be saved by the controller 102 as well, since the interferograms can allow for additional processing of the data without loss of SNR.

The spectrometer resolution can be anywhere from 0.25 $cm^{-1}$ to 32 $cm^{-1}$. A smaller range, e.g., 2 $cm^{-1}$ to 8 $cm^{-1}$ is used in some examples, however. Currently, about a 4 resolution, for example, appears to balance the need to separate similar compounds, while $cm^{-1}$ achieving high SNR.

The deconvolution algorithm executed by the controller 102 is designed to analyze the resultant spectra to determine the chemicals present and their respective concentrations and specifically, the quantity of contents of the inhalers 12 that have leaked into the chamber 110. In specific implementations, each compound, e.g., each gas or vapor to be analyzed has a stored calibration spectrum in the controller 102 that will be used to identify and quantify its presence. Known IR deconvolution algorithms can be used or adapted. Examples of suitable deconvolution techniques include but are not limited to those based on multiple regression analysis, linear or non-linear regressions, least squares analysis, partial least squares (PLS) analysis, inverse least squares analysis or other approaches.

Most FTIR computer analysis algorithms select several compounds or mixtures of compounds to analyze, for example, 2 to 20+ compounds or mixtures. The analysis can involve selecting a region of the spectrum to analyze each compound (where it absorbs). This step can be preset or selected by the controller 110 based on potential interferences. Multiple regions can be used for each compound to get more quantitative precision and a better qualitative prediction. However, in the present example, the analyte of interest is usually known or there are only a few potential analytes so that a matrix can use used for those analytes.

A feature important to many of the embodiments described here is a calibration library maintained by the controller 102, for example. With its use, calibrations only need to be collected once by the controller 102 (for a specific type of FTIR, spectrometer, laser system) and could be integrated with the spectroscopic component used. A test laboratory with multiple "like" instruments could rely on the same calibration, reducing or minimizing the need to calibrate the various instruments.

To obtain the calibration library, each potential compound of the contents is added to the sample cell at a couple of masses or concentrations (calibration curve) and multiple pressures. In the preferred embodiment, the system is run at or near atmospheric pressure. The spectral regions for analysis can be set by the instrument manufacturer, by the user or automatically, e.g., by specific software. Quantification regions can be included, as can other spectral regions in which the compound absorbs, to enable the software to rely on the information for any compound that is using that absorption region for quantification.

A calibration curve can be generated so that a quantitative regression analysis (e.g., linear, quadratic, or, as needed, cubic or quartic) can be performed.

Techniques described herein can be used to determine the integrity of pressurized containers during the manufacturing process, e.g., quality control stages, transport, storage or end use, in developing container designs, to meet compliance requirements, detect emissions of hazardous gases, e.g., from lecture bottles, to the environment, and so forth.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pressurized container testing system, comprising:
   a test chamber holding at least one pressurized container and accumulating an analyte leaking from the container;
   a sample cell receiving the analyte from the test chamber; and
   a spectrometry system for obtaining a spectral response of the analyte in the sample cell,
   wherein the at least one pressurized container is an inhaler.

2. The pressurized container testing system of claim 1, further comprising conduits defining a flow path for directing the analyte from the test chamber to the sample cell and returning the analyte from the sample cell to the test chamber.

3. The pressurized container testing system of claim 2, wherein the flow path includes a circulating pump.

4. The pressurized container testing system of claim 2, further comprising one or more valves disposed in the flow path.

5. The pressurized container testing system of claim 1, wherein the test chamber is connected to the sample cell through a closed loop flow path.

6. The pressurized container testing system of claim 1, further comprising a vacuum pumping device for evacuating or partially evacuating the sample cell.

7. The pressurized container testing system of claim 1, wherein the spectroscopy system determines the spectral response of the analyte in the sample cell in one or more of the following spectral regions: millimeter, microwave, terahertz, infrared (including near-, mid- and/or far-infrared), visible, ultraviolet (UV) (including vacuum ultraviolet (VUV)), x-rays and/or gamma.

8. The pressurized container testing system of claim 1, wherein the spectroscopy system measures absorption spectra, emission (including blackbody or fluorescence) spectra, elastic scattering and reflection spectra, impedance (e.g., index of refraction) spectra, and/or inelastic scattering (e.g., Raman and Compton scattering) spectra of the analyte in the sample cell.

9. The pressurized container testing system of claim 1, wherein the spectroscopy system is a Fourier transform infrared spectrometer.

10. The pressurized container testing system of claim 1, wherein a path length in the sample cell is increased by a multiple path optical arrangement.

11. A pressurized container testing system, comprising:
    a test chamber holding at least one pressurized container and accumulating an analyte leaking from the container;
    a sample cell receiving the analyte from the test chamber; and
    a spectrometry system for obtaining a spectral response of the analyte in the sample cell,
    wherein the sample cell includes a White cell or a modified White cell type optical arrangement.

12. The pressurized container testing system of claim 1, further comprising one or more instrument controls executing procedures for accessing information on known compounds, integration procedures, background correction procedures, compound information libraries, calibrations, internal standards, or any combinations thereof.

13. A pressurized container testing method, comprising:
accumulating an analyte leaking from at least one pressurized container;
analyzing spectral responses of the analyte accumulated from the at least one container,
wherein the at least one pressurized container is an inhaler.

14. The testing method of claim 13, wherein the analyte is directed from a test chamber to a sample cell and/or from the sample cell to the test chamber following a flow path.

15. The testing method of claim 14, the flow path is a closed loop flow path.

16. The testing method of claim 13, wherein the test chamber is connected to the sample cell through a closed loop flow path.

17. The testing method of claim 13, wherein analyzing the spectral responses comprises collecting the responses in one or more of the following spectral regions millimeter, microwave, terahertz, infrared (including near-, mid- and/or far-infrared), visible, ultraviolet (UV) (including vacuum ultraviolet (VUV)), x-rays and/or gamma.

18. The testing method of claim 13, wherein analyzing the spectral responses comprises obtaining absorption spectra, emission (including blackbody or fluorescence) spectra, elastic scattering and reflection spectra, impedance (e.g., index of refraction) spectra, and/or inelastic scattering (e.g., Raman and Compton scattering) spectra of the analyte in the sample cell.

19. The testing method of claim 13, wherein analyzing the spectral responses includes obtaining absorption spectra by Fourier transform infrared spectrometry.

20. The testing method of claim 13, wherein a path length in the sample cell is increased by a multiple path optical arrangement.

21. The testing method of claim 13, wherein the sample cell includes a White cell or modified White cell type optical arrangement.

22. The testing method of claim 13, further comprising executing one or more procedures for accessing information on known compounds, integration procedures, background correction procedures, compound information libraries, calibrations, internal standards, or any combinations thereof.

23. The testing method of claim 13, further comprising drawing at least a partial vacuum on the sample cell.

24. The testing method of claim 13, further comprising determining a difference between a starting point analyte concentration and an end point analyte concentration over a time period and calculating a leak rate for the pressurized container.

* * * * *